US007005548B2

(12) United States Patent
Choudhuri et al.

(10) Patent No.: US 7,005,548 B2
(45) Date of Patent: Feb. 28, 2006

(54) PROCESS FOR PREPARING QUATERNARY AMMONIUM TRIBROMIDES

(75) Inventors: Mihir Kanti Choudhuri, Assam (IN); Upasana Bora, Assam (IN); Sanjay Kumar Dehury, Assam (IN); Deepa Dey, Assam (IN); Siddhartha Sankar Dhar, Assam (IN); Wancydora Kharmawphlang, Assam (IN); Boyapati Manoranjan Choudhary, Andhra Pradesh (IN); Lakshmi Kantam Mannepalli, Andhar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 284 days.

(21) Appl. No.: 10/335,105

(22) Filed: Dec. 31, 2002

(65) Prior Publication Data
US 2004/0126308 A1    Jul. 1, 2004

(51) Int. Cl.
*C07C 209/00* (2006.01)
(52) U.S. Cl. .................................................. 564/296
(58) Field of Classification Search ................. 564/296
See application file for complete search history.

(56) References Cited

OTHER PUBLICATIONS

Bora et al., Pure and Applied Chemistry (2001), vol. 73, No. 1, p. 93-102.*
Chaudhuri M K et al: "An environmentally benign synthesis of organic ammonium tribromides (OATB) and bromination of selected organic substrates by tetrabutylammonium tribromide (TBATB)" Tetrahedron Letters, vol. 39, 1998, pp. 8163-8166, XP00413887.
Inokuchi T et al: "A new oxidising system for aromatic alcohols by the combination of N-Oxoammonium salt and electrosynthesised tetraalkylammonium tribromide" Bulletin of the Chemical Society of Japan, vol. 64, No. 3, 1991, pp. 796-800, XP009016891.
Buckles R E et al: "Spectrophotometric study of tetrabutylammonium tribromide" Journal of the American Cancer Society, vol. 73, No. 10, Oct. 19, 1951, pp. 4525-4528, XP002253837.
Avramoff M et al: "The brominating properties of tetramethylammonium tribromide" Journal of Organic Chemistry, vol. 28, No. 11, Nov. 1963, pp. 3256-3258, XP002253838.
Kajigaeshi S et al: "Synthesis of dibromoacetyl derivatives by use of benzyltrimethylammonium tribromide" Bulletin of the Chemical Society of Japan, vol. 60, No. 7, 1987, pp. 2667-2668, XP009016861.
Chattaway F D et al: "Perhalides of quaternary ammonium salts" Journal of the Chemical Society, vol. 123, 1923, pp. 654-662, XP009016856.
Database WPI Week 197419, Derwent Publications LTD., London, GB; AN 1974-35404V, XP002253839 "Quaternary ammonium tribromides"—&JP 49 014411 A (Nippon Soda Co.), Feb. 7, 1974.
Database WPI Week 198514, Derwent Publications Ltd., London, GB; AN 1985-085785, XP002253840, "Tetraethyl ammonium tribromide preparation"-& SU 1 113 374A (Moscow Lomonosov Univ), Sep. 15, 1984.

* cited by examiner

*Primary Examiner*—Brian Davis
(74) *Attorney, Agent, or Firm*—Darby & Darby

(57) ABSTRACT

The present invention relates to an economical and environmentally clean process for the preparation of high quality quaternary ammonium tribromides by oxidation of bromide ($Br^-$) in an acidic medium by a biomimetic process involving transition metal ion mediated activation of hydrogen peroxide.

13 Claims, No Drawings

PROCESS FOR PREPARING QUATERNARY AMMONIUM TRIBROMIDES

FIELD OF THE INVENTION

The present invention relates to an economical and environmentally clean process for the preparation of high quality quaternary ammonium tribromides. More particularly, this invention relates to quaternary ammonium salts of tribromides, having the general formula, QATB where QA is a quaternary ammonium cation selected from the group consisting of tetramethylammonium (TMA), tetraethylammonium (TEA), tetrabutylammonium (TBA), benzyltrimethylammonium (BTMA) and cetyltrimethylammonium (CTMA) and TB ($Br_3^-$) is the tribromide anion, obtained by the oxidation of bromide ($Br^-$) in an acidic medium by a biomimetic process involving transition metal ion mediated activation of hydrogen peroxide.

BACKGROUND OF THE INVENTION

Quaternaryammonium tribromides (QATBs) are highly efficient brominating agents. In other words, these reagents are capable of brominating organic substrates without the use of elemental bromine. QATBs act as vital reagents for preparation of bromoorganics which have anti inflammatory, anti viral (e.g., anti HIV), antineoplastic, antibacterial, and antifungal properties and are capable of acting as flame retardants, agrochemicals and other speciality products. The QATBs are regarded as 'solid bromine'.

The QATBs are widely used in the bromination of allyl alcohols, enones, alkenes, alkynes, activated aromatics such as anilines and phenols, polycyclic hydrocarbons such as anthracene and phenanthrene and sensitive substrates such as imidazole. They are also used as bifunctional catalysts in the oxidative bromination of aromatic compounds by aqueous hydrogen bromide/hydrogen peroxide, and diastereoselective bromination of allyl glycosides.

While the main claim of the reagents lies in their ability to act as brominating agents, the QATBs are versatile oxidizing agents as well. The reagents are used for selective oxidation of sulfides to sulfoxides, benzyl alcohols to benzaldehydes and benzoic acids, 1,4-benzenediols to 2,5-cyclohexadiene-1,4-diones and oxidation of formic and oxalic acids to carbon dioxide. The oxidation of phosphorus (I) and (III) oxyacids by QATBs leads to the formation of the corresponding phosphorus(III) and (V) oxyacids, respectively.

Highlighting the reagents' diverse uses, the QATBs can also be used efficiently for Hofinann degradation of amides, for methoxybromination of styrene and for the one-step synthesis of N-substituted acylureas and carbamates from amides. Moreover, some of the reagents, CTMATB have anti-bacterial properties as well. In an application of topical importance, these reagents have been shown to work as very effective brominating agents in solvent-free bromination of organic substrates.

Quaternary ammonium tribromides, also referred to as organic ammonium tribromides or organic tribromides or organic ammonium perbromides are well known in the art as witnessed for example by the incorporation of these bromides in the Encyclopedia of Reagents for Organic Synthesis, L. A. Paquette (Ed. in chief), 1995, John Wiley and Sons, Inc., New York and Reagents for Organic Synthesis, L. A. Fieser and M. Fieser, 1967, John Wiley and Sons, Inc., New York.

Reference is made to *J. Chem. Soc.*, 1923, 123, 654 and *J. Org. Chem.*, 1963, 28, 3256, wherein tetramethylammonium tribromide is prepared from tetramethylammonium bromide and bromine in acetic acid. The disadvantages are the toxic effects of bromine and the harsh reaction conditions. Reference is also made to Russian Pat. No. SU 1,113,374 (Cl. CO7C87/30), 15 Sep. 1984, 3,553,280, 28 Dec. 1982, wherein tetraethylammonium tribromide is produced by treating tetraethylammonium monobromide with a brominating agent consisting of a solution of an oxidizing agent such as Ce dioxide hydrate or ceric ammonium nitrate in HBr. The disadvantages are the use of toxic hydrobromic acid and production of heavy metal waste.

Reference is made to *J. Am. Chem. Soc.*, 1951, 73, 4525 wherein preparation of tetrabutylammonium tribromide was achieved by mixing a solution of tetrabutylammonium bromide in carbon tetrachloride with bromine. The disadvantages are the use of highly hazardous bromine and environmentally unacceptable toxic halo solvent. Reference is also made to *Bull. Chem. Soc. Jpn.*, 1987, 60, 2667 wherein benzyltrimethylammonium tribromide is prepared by adding aqueous HBr to a solution of benzyltrimethylammonium chloride and $NaBrO_3$ in water. The disadvantage is the use of environmentally hazardous hydrobromic acid. Reference is further made to Japanese Patent No. 74 14, 411 (Cl. 16 B314); 07 Feb. 1974, Appl. 72 58, 343, 12 Jun. 1972 wherein cetyltrimethylammonium tribromide was prepared by treating the corresponding monobromide with bromine in the presence of aqueous HBr. The disadvantages are the use of toxic chemicals like bromine and hydrobromic acid.

OBJECTS OF THE INVENTION

The main object of the present invention is to provide an improved economical and environmentally clean process for the synthesis of quaternary ammonium salts of tribromides, by the biomimetic oxidation of quaternary ammonium salts of bromide ($Br^-$) with a peroxo-metal intermediate and KBr in an acidic medium.

Another object of the invention is to provide a process for the synthesis of quaternary ammonium salts of tribromides where the use of bromine or HBr is completely avoided.

Another object of the invention is to provide a process for the synthesis of quaternary ammonium salts of tribromides where quaternary ammonium bromide (QAB) is used as the primary source of bromide.

Another object of the invention is to provide a process for the synthesis of quaternary ammonium salts of tribromides by oxidation of quaternary ammonium bromide (QAB) to quaternary ammonium tribromide (QATB).

Another object of the invention is to provide a process for the synthesis of quaternary ammonium salts of tribromides where bromide oxidation is conducted under mild conditions.

Yet another object of the invention is to provide a process for the synthesis of quaternary ammonium salts of tribromides where no organic solvent is needed for the reactions.

Another object of the invention is to provide a process for the synthesis of quaternary ammonium salts of tribromides where no waste is produced in the process.

Another object of the invention is to provide a process for the synthesis of quaternary ammonium salts of tribromides by reactions that are facile.

Another object of the invention is to provide a process for the synthesis of quaternary ammonium salts of tribromides where the desired products are obtained in very or quantitative yields.

Another object of the invention is to provide a process for the synthesis of quaternary ammonium salts of tribromides where the desired products obtained are pure and crystalline.

Yet another object of the invention is to provide a process for the synthesis of quaternary ammonium salts of tribromides which is cost-effective.

Yet another object of the invention is to provide a process for the synthesis of quaternary ammonium salts of tribromides wherein the products obtained are stable and have a long shelf life.

SUMMARY OF THE INVENTION

The novelty of the present invention resides in the development of an improved economical and environmentally clean process for the synthesis of quaternary ammonium salts of tribromides of the general formula, QATB where QA is a quaternary ammonium cation selected from the group consisting of tetramethylammonium (TMA), tetraethylammonium (TEA), tetrabutylammonium (TBA), benzyltrimethylammonium (BTMA) and cetyltrimethylammonium (CTMA) and TB ($Br_3^-$) is the tribromide anion, by the biomimetic oxidation of quaternary ammonium salts of bromide ($Br^-$) with a peroxo-metal intermediate and KBr in an acidic medium.

Accordingly, the present invention provides a process for preparing quaternary ammonium salts of tribromides of the formula QATB, wherein QA is a quaternary ammonium cation and TB ($Br_3^-$) is the tribromide anion, by the biomimetic oxidation of quaternary ammonium bromide ($Br^-$) with a peroxo-metal intermediate and KBr/$NH_4Br$ in an acidic medium.

In one embodiment of the invention, the quaternary ammonium cation is selected from the group consisting of tetramethylammonium (TMA), tetraethylammonium (TEA), tetrabutylammonium (TBA), benzyltrimethylammonium (BTMA) and cetyltrimethylammonium (CTMA).

In another embodiment of the invention, the reaction proceeds without the use of molecular bromine or direct use of HBr.

In another embodiment of the invention, the quaternary ammonium bromide (QAB) is used as the primary bromide source.

In yet another embodiment of the invention, the quaternary ammonium bromide (QAB) is oxidized to quaternaryammonium tribromide (QATB).

In yet another embodiment of the invention, the bromide oxidation is conducted under mild conditions.

In yet another embodiment of the invention, the oxidant used is aqueous hydrogen peroxide in stoichiometric amounts.

In a further embodiment of the invention, higher valence transition metal catalysts selected from V(V) and Mo(VI)) are used in catalytic amounts for activation of hydrogen peroxide.

In a further embodiment of the invention, the peroxo-transition metal is selected from the group consisting of V(V), Mo(VI), W(VI), Ti(IV), Cu(II), $UO_2^{2+}$ and any other metal capable of activating hydrogen peroxide.

In still another embodiment of the invention the use of metal ion renders hydrogen peroxide more reactive.

In another embodiment of the invention, the acidic medium is used as promoter for bromide oxidation.

In yet another embodiment of the invention, monobromide is converted to tribromide.

In a further embodiment of the invention, the acidic medium is selected from sulfuric acid and perchloric acid.

In yet another embodiment of the invention, one-third of the bromide is obtained from the quaternary ammonium bromide.

In another embodiment of the invention, two-third of the required bromide is obtained from a second bromide source.

In yet another embodiment of the invention, the second bromide source is selected from KBr and $NH_4Br$.

In a further embodiment of the invention, the reaction is carried out in the absence of an organic solvent.

DETAILED DESCRIPTION OF THE INVENTION

Although bromoorganics take a rather small share of the entire domain of organic chemistry, brominated organic products, especially bromoaromatics enjoy a very special status because of their use in the manufacture of a range of bulk and fine chemicals including flame-retardants, disinfectants, antibacterial and antiviral drugs. The commercial importance of organic bromo derivatives lies in their use as precursors in the manufacture of pharmaceuticals, agrochemicals and other specialty chemical products.

Recorded methods of synthesis that are largely used in practice involve elemental bromine ($Br_2$) because of its availability and versatility. There is an incentive to find out alternatives to the elemental bromine, since it is highly hazardous to the environment, detrimental to health, noxious and corrosive, which make its transportation, storage and handling extremely difficult. Moreover, the atom accountability in reactions involving bromine is terribly low with clear unquestionable trends of inefficiency and waste.

Interestingly, marine natural chemicals contain bromometabolites such as halogenated phenols, terpenes, C-15 acetogenins and indoles, for example, which are generated through enzyme catalyzed bromination of the metabolites. Studies have revealed that the enzyme responsible for these brominations is something that is called vanadium bromoperoxidase (VBrPO). It is also understood from the knowledge obtained from the structure and reactivity studies of VBrPO that the enzyme interacts first with $H_2O_2$ to activate the coordinated peroxide ligand so as to enable it oxidize bromide ($Br^-$) that is available in the marine natural system to produce active bromine species which in turn is responsible for bromination of organic substrates in the marine environment.

In addition to what has been reviewed above, the fact that hydrogen peroxide ($H_2O_2$) on being coordinated to a higher valent transition metal (e.g., V(V), Mo(VI), W(VI), Ti(IV), Cu(II) or $UO_2^{2+}$) gets activated to perform many reactions. What is equally interesting to note is that the metal, i.e., vanadium occurs in its pentavalent state in VBrPO and that it does not undergo any redox cycling in the catalytic bromination process.

Focus was given in the present investigation into bromide oxidation, the importance of bromoorganics as highlighted above, environmental problems associated with classical brominations by $Br_2$, and the capability of many peroxo complexes of Ti(IV), V(V), Mo(VI) and $UO_2^{2+}$ to oxidize Br very effectively in the presence of an acid. The process developed in the present investigation comprises the synthesis of quaternary ammonium salts of tribromides, having the general formula, QATB, a solid bromine, wherein QA is a quaternary ammonium cation selected from the group consisting of tetramethylammonium (TMA), tetraethylammonium (TEA), tetrabutylammonium (TBA), benzyltrimethylammonium (BTMA) and cetyltrimethyl-ammonium (CTMA) and TB ($Br_3^-$) is the tribromide anion, obtained in quantitative yields in a reaction comprising the biomimetic oxidation of quaternary ammonium bromide (Br⁻) with a peroxo-metal intermediate and KBr/NH₄Br in an acidic medium.

The use of molecular bromine and the direct use of HBr in the reaction is completely avoided. Instead, the quaternaryammonium bromide (QAB) is used as the primary source of bromide. If desired, a secondary source of bromide such as KBr or NH₄Br or any other appropriate bromide. The quaternaryammonium bromide (QAB) is oxidized to quaternaryammonium tribromide (QATB) with the bromide oxidation being conducted under mild conditions. When both a primary and secondary source of bromide are used, one-third of the bromide is preferably derived from the quaternary ammonium bromide and two-third is afforded by the secondary source of bromide. KBr is preferred as the secondary source of bromide since it is a cheap source of bromide.

The oxidant used is aqueous hydrogen peroxide which is environmentally benign oxidant, in stoichiometric amounts. Higher valent transition metal catalysts V(V) and Mo(VI) are used in catalytic amounts for activation of hydrogen peroxide. The peroxo-transition metal is selected from V(V), Mo(VI), W(VI), Ti(IV), Cu(II), UO$_2^{2+}$ or any other metal capable of activating hydrogen peroxide. The use of the metal ion renders hydrogen peroxide more reactive. The acidic medium itself is used as promoter for bromide oxidation. The acids are preferably chosen from sulfuric acid and perchloric acid. The reaction proceeds due to the conversion of monobromide is converted to tribromide.

No organic solvent is needed for the reactions. Another significant advantage is that not only is no waste is produced in the process, the reactions are rapid and facile with products being obtained in high or quantitative yields without requiring any recrystallization. QATBs obtained by the process of the invention are comparatively far more stable and have a long shelf life since no HBr is used in the processes.

SCIENTIFIC EXPLANATION

The principle of the present invention is to prepare quaternaryammonium tribromides by novel, economic and environmentally clean processes. The scientific philosophy behind these principles is depicted in scheme 1:

Scheme 1
Mechanistic Pathway for QATB Synthesis

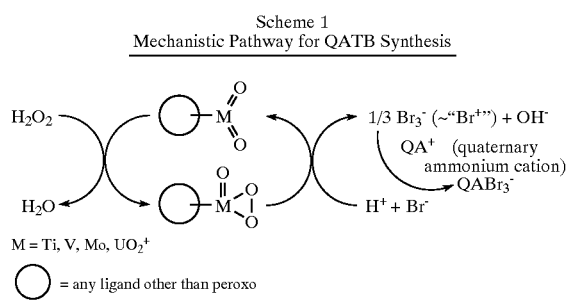

The mechanism (Scheme 1) may be explained in terms of the following steps:

(i) Activation of peroxide through coordination to a higher valent metal ion.

(ii) Opening up of the peroxo ring in the presence of acid. (not shown in the scheme)

(iii) Oxidation of bromide.

(iv) Isolation of Br₃— from solution by precipitation with a heavy cation.

Two general protocols have been developed to provide easy accesses to the commercially important quaternaryammonium tribromides. Thus we have disclosed herein two different methods of preparation of QATBs, viz., Protocol A and Protocol B. Though the two methods are apparently similar, the Protocol A differs from the Protocol B in terms of the quantity of water used in the two preparations. Each method has an advantage over the other.

Protocol A uses an excess of water to help remove the soluble salt(s) but affording the products in slightly lower yields, Scheme 2

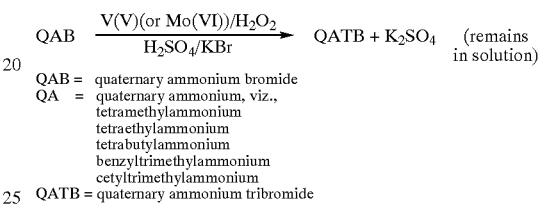

QAB = quaternary ammonium bromide
QA = quaternary ammonium, viz.,
 tetramethylammonium
 tetraethylammonium
 tetrabutylammonium
 benzyltrimethylammonium
 cetyltrimethylammonium
QATB = quaternary ammonium tribromide Protocol B uses only a restricted quantity of water that owes its origin to the hydrogen peroxide and acid solutions. This provides a more effective interaction among the reactants and averts any loss due to solubility of QATBs. However, one extraction step is necessary in order to render QATBs free from the salt of the acid.

Scheme 3

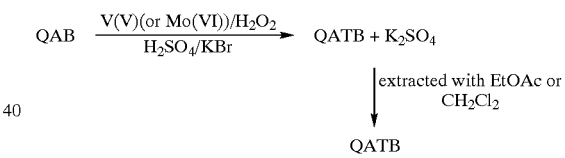

QAB = quaternary ammonium bromide
QA = quaternary ammonium, viz.,
 tetramethylammonium
 tetraethylammonium
 tetrabutylammonium
 benzyltrimethylammonium
 cetyltrimethylammonium
QATB = quaternary ammonium tribromide The following examples are given by way illustration and therefore should not be construed to limit the scope of the invention.

Protocol A is applied for examples 1 to 5 and Protocol B for examples 6 to 10.

EXAMPLE 1

Synthesis of Tetramethylammonium Tribromide, TMATB (from TMAB)

A sample of molybdic acid monohydrate, $H_2MoO_4.H_2O$ (0.32 mmol, 0.058 g) was taken in a 250 mL glass beaker and 30% hydrogen peroxide, $H_2O_2$ (176.37 mmol, 20 mL) was added to it. The mixture was stirred for 30 min at room temperature. The solution, which was slightly turbid, was filtered through Whatman No. 1 filter paper on a glass funnel.

The clear filtrate was collected in a 250 mL glass beaker and kept in an ice-water bath. Tetramethylammonium bromide, TMAB (32.45 mmol, 5 g) and potassium bromide, KBr (129.83 mmol, 15.45 g) dissolved in (0.8M) $H_2SO_4$ (40 mmol, 50 mL) was added to this solution slowly with continuous stirring leading to the formation of a golden colored precipitate.

The mixture was continued to stir in ice-water bath for another ~1 h and then kept standing in ice-water bath for 2 h to get an orange yellow compound of Tetramethylammonium tribromide, TMATB. The compound was separated by filtration under suction using Whatman No. 1 filter paper. It was dried in vacuo over fused $CaCl_2$ and was recrystallized from acetonitrile.

Yield=9.35 g (91.79%) MP: 119° C. The chemical analyses, IR and conductance of the compound match very well with those reported in literature. Analytical data: The compound analyzed correctly $C_4H_{12}NBr_3$: Calc. C, 15.31; H, 3.85; N, 4.46; Br, 76.38%. Found. C, 15.29; H, 3.86; N, 4.45; Br, 76.4%.

EXAMPLE 2

Synthesis of Tetramethylammonium Tribromide, TMATB (from TMAC)

A sample of molybdic acid monohydrate, $H_2MoO_4.H_2O$ (0.46 mmol, 0.082 g) was taken in a 250 mL glass beaker and 30% hydrogen peroxide, $H_2O_2$ (264.55 mmol, 30 mL) was added to it. The mixture was stirred for 30 min at room temperature. The solution, which was slightly turbid, was filtered through Whatman No. 1 filter paper on a glass funnel. The clear filtrate was collected in a 250 mL glass beaker and kept in an ice-water bath. Tetramethylammonium chloride, TMAC (45.61 mmol, 5 g) and potassium bromide, KBr (268.91 mmol, 32 g) dissolved in (1 M) $H_2SO_4$ (100 mmol, 100 mL) was added to this solution slowly with continuous stirring leading to the formation of a yellow precipitate. The mixture was continued to stir in ice-water bath for another ~1 h and then kept standing in ice-water bath for 2 h to get an orange yellow compound of Tetramethylammonium tribromide, TMATB. The compound was separated by filtration under suction using Whatman No. 1 filter paper. It was dried in vacuo over fused $CaCl_2$ and was recrystallized from acetonitrile.

Y=13.35 g (93.25%) MP: 119° C. The chemical analyses, IR and conductance of the compound match very well with those reported in literature. Analytical data: The compound analyzed correctly $C_4H_{12}NBr_3$: Calc. C, 15.31; H, 3.85; N, 4.46; Br, 76.38%. Found. C, 15.29; H, 3.86; N, 4.45; Br, 76.4%.

EXAMPLE 3

Synthesis of Tetraethylammonium Tribromide, TEATB (from TEAB)

A sample of molybdic acid monohydrate, $H_2MoO_4.H_2O$ (0.24 mmol 0.043 g) was taken in a 250 mL glass beaker and 30% hydrogen peroxide, $H_2O_2$ (23.81 mmol, 2.7 mL) was added to it. The mixture was stirred for 30 min at room temperature. The solution, which was slightly turbid, was filtered through Whatman No. 1 filter paper on a glass funnel. The clear filtrate was collected in a 250 mL glass beaker and kept in an ice-water bath. Tetraethylammonium bromide, TEAB (23.79 mmol, 5 g) and potassium bromide, KBr (47.56 mmol. 5.66 g) dissolved in (0.5M) $H_2SO_4$ (23.79 mmol. 47.58 mL) was added to this solution slowly with continuous stirring leading to the formation of a yellow precipitate. The mixture was continued to stir in ice-water bath for another ~1 h and then kept standing in ice-water bath for 2 h to get an orange yellow compound of Tetraethylammonium tribromide, TEATB. The compound was separated by filtration under suction using Whatman No. 1 filter paper. It was dried in vacuo over fused $CaCl_2$ and was recrystallized from acetonitrile.

Y=8.36 g (94.99%) MP: 86–87° C. The chemical analyses, IR and conductance of the compound match very well with those reported in literature. Analytical data: The compound analyzed correctly $C_8H_{20}NBr_3$: Calc. C, 25.97; H, 5.45; N, 3.79; Br, 64.79%. Found. C, 25.99; H, 5.82; N, 3.67; Br, 64.52%.

EXAMPLE 4

Synthesis of Tetrabutylammonium Tribromide, TBATB (from TBAB)

A sample of molybdic acid monohydrate, $H_2MoO_4.H_2O$ (0.16 mmol, 0.029 g) was taken in a 250 mL glass beaker and 30% hydrogen peroxide, $H_2O_2$ (15.52 mmol, 1.76 mL) was added to it. The mixture was stirred for 30 min. at room temperature. The solution, which was slightly turbid, was filtered through Whatman No. 1 filter paper on a glass funnel. The clear filtrate was collected in a 250 mL glass beaker and kept in the ice-water bath. Tetrabutylammonium bromide, TBAB (15.51 mmol, 5 g) and potassium bromide, KBr (31.01 mmol, 3.69 g) dissolved in (0.3M) $H_2SO_4$ (15.52 mmol, 51.70 mL) was added to this solution slowly with continuous stirring leading to the formation of a yellow precipitate. The mixture was continued to stir in ice-water bath for another ~1 h and then kept standing in ice-water bath for 2 h to get an orange yellow compound of Tetrabutylammonium tribromide, TBATB. The compound was separated by filtration under suction using Whatman No. 1 filter paper. It was dried in vacuo over fused $CaCl_2$ and was recrystallized from acetonitrile.

Y=7.23 g (96.7%) MP: 76–77° C. The chemical analyses, IR and conductance of the compound match very well with those reported in literature. Analytical data: The compound analyzed correctly $C_{16}H_{36}NBr_3$: Calc. C, 39.86; H, 7.52; N, 2.90; Br, 49.71%. Found. C, 39.41; H, 8.28; N, 2.78; Br, 49.53%.

EXAMPLE 5

Synthesis of Cetyltrimethylammonium Tribromide, CTMATB (from CTMAB)

A sample of molybdic acid monohydrate, $H_2MoO_4.H_2O$ (0.14 mmol, 0.025 g) was taken in a 250 mL glass beaker and 30% hydrogen peroxide, $H_2O_2$ (13.76 mmol, 1.56 mL) was added to it. The mixture was stirred for 30 min. at room temperature. The solution, which was slightly turbid, was filtered through Whatman No. 1 filter paper on a glass funnel. The clear filtrate was collected in a 250 mL glass beaker and kept in the ice-water bath. Cetyltrimethylammonium bromide, CTMAB (13.72 mmol, 5 g) and potassium bromide, KBr (27.48 mmol, 3.27 g) dissolved in (0.3M) $H_2SO_4$ (13.72 mmol, 45.73 mL) was added to this solution slowly with continuous stirring leading to the formation of a yellow precipitate. The mixture was continued to stir in ice-water bath for another ~1 h and then kept standing in ice-water bath for 2 h to get an orange yellow compound of Cetyltrimethylammonium tribromide, CTMATB. The compound was separated by filtration under suction using Whatman No. 1 filter paper. It was dried in vacuo over fused CaCl$_2$ and was recrystallized from acetonitrile.

Y=7.11 g (98.86%) MP: 86–87° C. The chemical analyses, IR and conductance of the compound match very well with those reported in literature. Analytical data: The compound analyzed correctly C$_{19}$H$_{42}$NBr$_3$: Calc. C, 43.53; H, 8.07; N, 2.67; Br, 45.72%. Found. C, 40.99; H, 7.91; N, 2.74; Br, 48.36%.

EXAMPLE 6

Synthesis of Tetraethylammonium Tribromide, TEATB (from TEAB)

Molybdic acid monohydrate, H$_2$MoO$_4$.H$_2$O (0.24 mmol, 0.043 g), potassium bromide, KBr (47.56 mmol, 5.66 g) and tetraethylammonium bromide, TEAB (23.79 mmol, 5 g) were powdered separately, mixed together smoothly and thoroughly. The whole was transferred to a boat kept on ice-water bath and 30% hydrogen peroxide, H$_2$O$_2$ (23.81 mmol, 2.7 mL) was added drop wise with continuous grinding for 15 min, followed by drop wise addition of 10M H$_2$SO$_4$ (23.80 mmol, 2.38 mL) leading to the formation of a yellow colored solution. It was stirred smoothly with glass rod for 10 min and then at room temperature for 30 min. An exothermic reaction set in to form orange-yellow crystalline compound of tetraethylammonium tribromide, TEATB. The compound was dried over fused CaCl$_2$ and extracted with ethyl acetate by dissolving in minimum amount of solvent followed by filtration through Whatman No. 42 filter paper. Aqueous phase, if present, could be separated using anhydrous sodium sulphate. The organic layer was concentrated to get yellow-orange tetraethylammonium tribromide, TEATB and the latter was recrystallized from acetonitrile.

Yield: 8.44 g (95.89%) Mp: 86–87° C. The chemical analyses, IR and conductance of the compound match very well with those reported in literature. Analytical data: The compound analyzed correctly C$_8$H$_{20}$NBr$_3$: Calc. C, 25.97; H, 5.45; N, 3.79; Br, 64.79%. Found. C, 25.99; H, 5.82; N, 3.67; Br, 64.52%.

EXAMPLE 7

Synthesis of Tetrabutylammonium Tribromide, TBATB (From TBAB)

Molybdic acid monohydrate, H$_2$MoO$_4$.H$_2$O (0.16 mmol, 0.029 g), potassium bromide, KBr (31.01 mmol, 3.69 g) and tetrabutylammonium bromide, TBAB (15.51 mmol, 5 g) were powdered separately, mixed together smoothly and thoroughly. The whole was transferred to a boat kept on ice-water bath and 30% hydrogen peroxide, H$_2$O$_2$ (15.52 mmol, 1.76 mL) was added drop wise with continuous grinding for 15 min, followed by drop wise addition of 10 M H$_2$SO$_4$ (15.5 mmol, 1.55 mL) leading to the formation of a yellow colored solution. It was stirred smoothly with glass rod for 10 min and then at room temperature for 30 min. An exothermic reaction set in to form orange-yellow crystalline compound of tetrabutylammonium tribromide, TBATB. The compound was dried over fused CaCl$_2$ and extracted with ethyl acetate by dissolving in minimum amount of solvent followed by filtration through Whatman No. 42 filter paper. Aqueous phase, if present, could be separated using anhydrous sodium sulphate. The organic layer was concentrated to get yellow-orange tetrabutylammonium tribromide, TBATB and the latter was recrystallized from acetonitrile.

Yield: 7.2 g (96.26%) Mp: 76–77° C. The chemical analyses, IR and conductance of the compound match very well with those reported in literature. Analytical data: The compound analyzed correctly C$_{16}$H$_{36}$NBr$_3$: Calc. C, 39.86; H, 7.52; N, 2.90; Br, 49.71%. Found. C, 39.41; H, 8.28; N, 2.78; Br, 49.53%.

EXAMPLE 8

Synthesis of Benzyltrimethylammonium Tribromide, BTMATB (from BTMAB)

Molybdic acid monohydrate, H$_2$MoO$_4$.H$_2$O (0.13 mmol, 0.023 g), potassium bromide, KBr (26.06 mmol, 3.1 g) and benzyltrimethylammonium bromide, BTMAB (13.03 mmol, 3.0 g) were powdered separately, mixed together smoothly and thoroughly. The whole was transferred to a boat kept on ice-water bath and 30% hydrogen peroxide, H$_2$O$_2$ (13.23 mmol, 1.5 mL) was added drop wise with continuous grinding for 15 min, followed by drop wise addition of 10M H$_2$SO$_4$ (13.0 mmol, 1.3 mL) leading to the formation of a yellow colored solution. It was stirred smoothly with glass rod for 10 min and then at room temperature for 30 min. An exothermic reaction set in to form orange-yellow crystalline compound of benzyltrimethylammonium tribromide, BTMATB. The compound was dried over fused CaCl$_2$ and extracted with ethyl acetate by dissolving in minimum amount of solvent followed by filtration through Whatman No. 42 filter paper. Aqueous phase, if present, could be separated using anhydrous sodium sulphate. The organic layer was concentrated to get yellow-orange benzyltrimethylammonium tribromide, BTMATB. Yield: 4.17 g (82.04%) Mp: 98–101° C. The chemical analyses, IR and conductance of the compound match very well with those reported in literature.

Analytical data: The compound analyzed correctly C$_{10}$H$_{16}$NBr$_3$: Calc. C, 30.8; H, 4.14; N, 3.59; Br, 61.47%. Found. C, 30.7; H, 4.18; N, 3.62; Br, 61.53%.

EXAMPLE 9

Synthesis of Benzyltrimethylammonium Tribromide, BTMATB (from BTMAC)

Molybdic acid monohydrate, H$_2$MoO$_4$.H$_2$O (0.27 mmol, 0.049 g), potassium bromide, KBr (83.36 mmol, 9.92 g) and benzyltrimethylammonium chloride, BTMAC (26.92 mmol, 5 g) were powdered separately, mixed together smoothly and thoroughly. The whole was transferred to a boat kept on ice-water bath and 30% hydrogen peroxide, H$_2$O$_2$ (40.56 mmol, 4.6 mL) was added drop wise with continuous grinding for 15 min, followed by drop wise addition of 10 M H$_2$SO$_4$ (40.6 mmol, 4.06 mL) leading to the formation of a yellow colored solution. It was stirred smoothly with glass rod for 10 min and then at room temperature for 30 min. An exothermic reaction set in to form orange-yellow crystalline compound of benzyltrimethylammonium tribromide, BTMATB. The compound was dried over fused CaCl$_2$ and extracted with ethyl acetate by dissolving in minimum amount of solvent followed by filtration through Whatman No. 42 filter paper. Aqueous phase, if present, could be separated using anhydrous sodium sulphate. The organic layer was concentrated to get yellow-orange benzyltrimethylammonium tribromide, BTMATB. Yield: 10 g (95.25%) Mp: 99–101° C. The chemical analyses, IR and conductance of the compound match very well with those reported in literature.

Analytical data: The compound analyzed correctly $C_{10}H_{16}NBr_3$: Calc. C, 30.8; H, 4.14; N, 3.59; Br, 61.47%. Found. C, 30.7; H, 4.18; N, 3.62; Br, 61.53%.

EXAMPLE 10

Synthesis of Cetyltrimethylammonium Tribromide, CTMATB (from CTMAB)

Molybdic acid monohydrate, $H_2MoO_4.H_2O$ (0.14 mmol, 0.025 g), potassium bromide, KBr (27.48 mmol, 3.27 g) and cetyltrimethylammonium bromide, CTMAB (13.72 mmol, 5 g) were powdered separately, mixed together smoothly and thoroughly. The whole was transferred to a boat kept on ice-water bath and 30% hydrogen peroxide, $H_2O_2$ (13.76 mmol, 1.56 mL) was added drop wise with continuous grinding for 15 min, followed by drop wise addition of 10M $H_2SO_4$ (13.72 mmol, 1.372 mL) leading to the formation of a yellow colored solution. It was stirred smoothly with glass rod for 10 min and then at room temperature for 30 min. An exothermic reaction set in to form orange-yellow crystalline compound of cetyltrimethylammonium tribromide, CTMATB. The compound was dried over fused $CaCl_2$ and extracted with dichloromethane by dissolving in minimum amount of solvent followed by filtration through Whatman No. 42 filter paper. Aqueous phase, if present, could be separated using anhydrous sodium sulphate. The organic layer was concentrated to get yellow-orange cetyltrimethylammonium tribromide, CTMATB and the latter was recrystallized from acetonitrile. Yield: 7.17 g (99.7%) Mp: 86–87° C. The chemical analyses, IR and conductance of the compound match very well with those reported in literature.

Analytical data: The compound analyzed correctly $C_{19}H_4Br_3$: Calc. C, 43.53; H, 8.07; N, 2.67; Br, 45.72%. Found. C, 42.99; H, 7.91; N, 2.74; Br, 46.36%.

ADVANTAGES OF THE INVENTION

The major advantages of the present invention are as follows:
1. The process is economical.
2. The newer methodology is environmentally clean and safe to operate.
3. The use of $Br_2$ and HBr is completely avoided.
4. The method of preparation is very facile.
5. No wastes are produced.
6. The process provides a high quality product.
7. The process is ecofriendly.

We claim:

1. A process for preparing quaternary ammonium salts of tribromides of the formula QATB, wherein QA is a quaternary ammonium cation and TB ($Br_3^-$) is the tribromide anion, said process comprising biomimetic oxidation of quaternary ammonium bromide ($Br^-$) as a primary bromide source, with a peroxo-metal intermediate and a second bromide source in an acidic medium, wherein about one-third of the bromide is obtained from the quaternary ammonium bromide.

2. The process as claimed in claim 1 wherein the quaternary ammonium cation is selected from the group consisting of tetramethylammonium (TMA), tetraethylammonium (TEA), tetrabutylammonium (TBA), benzyltrimethylammonium (BTMA) and cetyltrimethylammonium (CTMA).

3. The process as claimed in claim 1 wherein the reaction proceeds without the use of molecular bromine.

4. The process as claimed in claim 1 wherein the reaction proceeds without the use of HBr.

5. The process as claimed in claim 1 wherein the oxidation is conducted under mild conditions.

6. The process as claimed in claim 1 wherein the oxidant used is aqueous hydrogen peroxide in stoichiometric amounts.

7. The process as claimed in claim 6 wherein higher valence transition metal catalysts selected from V(V) and Mo(VI) are used in catalytic amounts for activation of hydrogen peroxide.

8. The process as claimed in claim 1 wherein the peroxo-metal intermediate is selected from the group consisting of V(V), Mo(VI), W(VI), Ti(IV), Cu(II) and $UO_2^{2+}$.

9. The process as claimed in claim 1 wherein the acidic medium is selected from sulfuric acid and perchloric acid.

10. The process as claimed in claim 1 wherein two-thirds of the required bromide is obtained from the second bromide source.

11. The process as claimed in claim 1, wherein the second bromide source is selected from KBr and $NH_4Br$.

12. The process as claimed in claim 1 wherein the reaction is carried out in the absence of an organic solvent.

13. A process for the synthesis of quaternary ammonium salts of tribromides of the formula QATB, wherein QA is a quaternary ammonium cation selected from the group consisting of tetramethylammonium (TMA), tetraethylammonium (TEA), tetrabutylammonium (TBA), benzyltrimethylammonium (BTMA) and cetyltrimethyl-ammonium (CTMA) and TB ($Br_3^-$) is the tribromide anion, said process comprising biomimetic oxidation of quaternary ammonium bromide ($Br^-$) as a primary bromide source, with a peroxo-metal intermediate and a second bromide source in an acidic medium, wherein about one-third of the bromide is obtained from the quaternary ammonium bromide.

* * * * *